United States Patent [19]
Pinchuk et al.

[11] Patent Number: 5,968,091
[45] Date of Patent: Oct. 19, 1999

[54] STENTS AND STENT GRAFTS HAVING ENHANCED HOOP STRENGTH AND METHODS OF MAKING THE SAME

[75] Inventors: Leonard Pinchuk, Miami, Fla.; Noureddine Frid, Beersel, Belgium

[73] Assignee: Corvita Corp., Miami, Fla.

[21] Appl. No.: 08/979,278

[22] Filed: Nov. 26, 1997

Related U.S. Application Data

[63] Continuation of application No. 08/622,709, Mar. 26, 1996, abandoned.

[51] Int. Cl.$^6$ ........................................... A61F 2/06
[52] U.S. Cl. ................................. 623/1; 600/36; 427/2.24
[58] Field of Search ..................... 623/1, 11, 12; 606/191, 194, 195, 198; 600/36; 427/2.1, 2.24

[56] References Cited

U.S. PATENT DOCUMENTS

| | | |
|---|---|---|
| 1,920,495 | 8/1933 | Brown et al. . |
| 2,836,181 | 5/1958 | Tapp . |
| 2,977,839 | 4/1961 | Koch . |
| 3,095,017 | 6/1963 | Bleiler et al. . |
| 3,105,492 | 10/1963 | Jeckel . |
| 3,272,204 | 9/1966 | Artandi et al. . |
| 3,304,557 | 2/1967 | Polansky . |
| 3,317,924 | 5/1967 | Le Veen et al. . |

(List continued on next page.)

FOREIGN PATENT DOCUMENTS

| | | |
|---|---|---|
| 0 312 852 | 4/1989 | European Pat. Off. . |
| 0 587 197 | 10/1991 | European Pat. Off. . |
| 0 621 015 A1 | 10/1994 | European Pat. Off. ................... 623/1 |
| 0621015 | 10/1994 | European Pat. Off. ................... 623/1 |
| 1 602 513 | 1/1970 | France . |
| 30 19 996 | 12/1981 | Germany . |
| 2 015 118 | 9/1879 | United Kingdom . |
| 1 205 743 | 9/1970 | United Kingdom . |
| 2 033 233 | 5/1980 | United Kingdom . |
| 2 077 107 | 12/1981 | United Kingdom . |
| 2 135 585 | 3/1986 | United Kingdom . |
| 2135585 | 3/1986 | United Kingdom ................... 623/1 |
| WO88/00813 | 2/1988 | WIPO . |
| WO91/12779 | 9/1991 | WIPO . |
| WO94/24961 | 11/1994 | WIPO . |

OTHER PUBLICATIONS

"A Study of the Geometrical and Mechanical Properties of a Self–Expanding Metallic–Stent . . . " Jedwab et al, Jour. of Applied Biomaterials, Vo. 4, pp.77–85 1993.

"Oesophageal Strictures" Didcott, Annals of the Royal Cllege of Surgeons of England, vol. 55, pp. 112–126, Aug. 1973.

*Primary Examiner*—Mickey Yu
*Assistant Examiner*—Tram A. Nguyen
*Attorney, Agent, or Firm*—David P. Gordon; David S. Jacobson; Thomas A. Gallagher

[57] ABSTRACT

Stents are coated with a polymer such that the polymeric coating binds the crossover points of the wires, or, in the case of a zig-zag stent, binds adjacent zig-zags of wires without occluding the interstices of the stent lattice. Suitable polymers include polyurethane, polycarbonate urethane, polyurethane urea, silicone rubber, polyisobutylene copolymer (with styrene, etc.), polyolefin, polyester, glycolated polyester, polyamide, amorphous polyamide, combinations of the above and the like. Biodegradable polymers such as polyisobuterate, polyvalerate, polylactic acid, polyglycolic acid and combinations of these are also suitable. The polymer can be reacted in place without a solvent, such as two component polyurethanes, or silicone rubbers, or the reacted polymer can be dissolved in an appropriate solvent, for example, dimethylacetamide for the polyurethanes, toluene for the polyolefins, or heptane for the silicone rubbers. In order to enhance bonding of the polymer to the stent wires, the metallic stent can be primed prior to coating. The hoop strength of a polymer coated stent is improved due to locking of the crossover points and preventing free motion of the stent wires relative to each other.

3 Claims, 4 Drawing Sheets

U.S. PATENT DOCUMENTS

| | | |
|---|---|---|
| 3,463,158 | 8/1969 | Schmitt et al. . |
| 3,479,670 | 11/1969 | Medell . |
| 3,485,234 | 12/1969 | Stevens . |
| 3,509,883 | 5/1970 | Diebelius . |
| 3,526,906 | 9/1970 | De Laszlo . |
| 3,562,820 | 2/1971 | Braun . |
| 3,580,289 | 5/1971 | James, Jr. . |
| 3,585,707 | 6/1971 | Stevens . |
| 3,626,947 | 12/1971 | Sparks . |
| 3,710,777 | 1/1973 | Sparks . |
| 3,730,835 | 5/1973 | Leeper . |
| 3,822,238 | 7/1974 | Blair et al. . |
| 3,868,956 | 3/1975 | Alfidi et al. . |
| 3,878,565 | 4/1975 | Sauvage . |
| 3,929,126 | 12/1975 | Corsaut . |
| 3,974,526 | 8/1976 | Dardik et al. . |
| 3,993,078 | 11/1976 | Bergentz et al. . |
| 4,044,404 | 8/1977 | Martin et al. . |
| 4,086,665 | 5/1978 | Poirier . |
| 4,106,129 | 8/1978 | Carpentier et al. . |
| 4,130,904 | 12/1978 | Whalen . |
| 4,134,402 | 1/1979 | Mahurkar . |
| 4,140,126 | 2/1979 | Choudhury . |
| 4,164,045 | 8/1979 | Bokros et al. . |
| 4,173,689 | 11/1979 | Lyman et al. . |
| 4,193,138 | 3/1980 | Okita . |
| 4,323,071 | 4/1982 | Simpson et al. . |
| 4,355,426 | 10/1982 | MacGregor . |
| 4,441,215 | 4/1984 | Kaster . |
| 4,459,252 | 7/1984 | MacGregor . |
| 4,475,972 | 10/1984 | Wong . |
| 4,503,569 | 3/1985 | Dotter . |
| 4,583,968 | 4/1986 | Mahurkar . |
| 4,610,688 | 9/1986 | Silvestrini et al. . |
| 4,655,771 | 4/1987 | Wallsten . |
| 4,692,141 | 9/1987 | Mahurkar . |
| 4,731,073 | 3/1988 | Robinson . |
| 4,743,251 | 5/1988 | Barra . |
| 4,776,337 | 10/1988 | Palmaz ........................ 623/1 |
| 4,787,899 | 11/1988 | Lazarus . |
| 4,850,999 | 7/1989 | Planck . |
| 4,871,357 | 10/1989 | Hsu . |
| 4,875,480 | 10/1989 | Imbert . |
| 4,878,906 | 11/1989 | Lindemann et al. . |
| 4,895,561 | 1/1990 | Mahurkar . |
| 4,935,006 | 6/1990 | Hasson . |
| 4,954,126 | 9/1990 | Wallsten . |
| 5,019,090 | 5/1991 | Pinchuk . |
| 5,026,377 | 6/1991 | Burton et al. . |
| 5,061,275 | 10/1991 | Wallsten et al. . |
| 5,064,435 | 11/1991 | Porter . |
| 5,078,720 | 1/1992 | Burton et al. . |
| 5,116,360 | 5/1992 | Pinchuk et al. . |
| 5,133,742 | 7/1992 | Pinchuk ........................ 623/1 |
| 5,160,641 | 11/1992 | Brenneman et al. . |
| 5,176,907 | 1/1993 | Leong ........................ 424/423 |
| 5,188,593 | 2/1993 | Martin . |
| 5,197,978 | 3/1993 | Hess . |
| 5,201,757 | 4/1993 | Heyn et al. . |
| 5,229,431 | 7/1993 | Pinchuk ........................ 623/66 |
| 5,235,966 | 8/1993 | Jamner . |
| 5,242,399 | 9/1993 | Lau et al. . |
| 5,279,561 | 1/1994 | Roucher et al. . |
| 5,290,295 | 3/1994 | Querals et al. . |
| 5,312,415 | 5/1994 | Palermo . |
| 5,330,500 | 7/1994 | Song . |
| 5,342,348 | 8/1994 | Kaplan ........................ 606/198 |
| 5,360,397 | 11/1994 | Pinchuk . |
| 5,360,443 | 11/1994 | Barone et al. ........................ 623/1 |
| 5,383,892 | 1/1995 | Cardon et al. . |
| 5,395,390 | 3/1995 | Simon et al. . |
| 5,397,355 | 3/1995 | Marin et al. . |
| 5,405,378 | 4/1995 | Strecker . |
| 5,415,664 | 5/1995 | Pinchuk . |
| 5,433,723 | 7/1995 | Lindenberg et al. . |
| 5,443,495 | 8/1995 | Buscemi et al. ........................ 623/1 |
| 5,476,508 | 12/1995 | Amstrup ........................ 606/191 |
| 5,503,636 | 4/1996 | Schmitt et al. ........................ 623/1 |
| 5,545,208 | 8/1996 | Wolff et al. ........................ 623/12 |
| 5,545,211 | 8/1996 | An et al. ........................ 623/1 |
| 5,556,414 | 9/1996 | Turi ........................ 606/198 |
| 5,601,593 | 2/1997 | Freitag ........................ 623/1 |

STENTS AND STENT GRAFTS HAVING ENHANCED HOOP STRENGTH AND METHODS OF MAKING THE SAME

This is a continuation of U.S. Ser. No. 08/622,709, filed Mar. 26, 1996 and now abandoned.

BACKGROUND OF THE INVENTION

1. Field of the Invention

The invention relates to self expanding stents and stent-grafts. More particularly, the invention relates to stents and stent-grafts with the stent having a polymeric coating which provides enhanced hoop strength as well as other benefits.

2. State of the Art

Transluminal prostheses are well known in the medical arts for implantation in blood vessels, biliary ducts, or other similar organs of the living body. These prostheses are commonly known as stents and are used to maintain, open, or dilate tubular structures or to support tubular structures that are being anastomosed. When biocompatible materials are used as a covering or lining for the stent, the prosthesis is called a stent-graft. If used specifically in blood vessels, the stent-graft is known as an endovascular graft. A stent or stent-graft may be introduced into the body by stretching it longitudinally or compressing it radially, until its diameter is reduced sufficiently so that it can be fed into a catheter. The stent-graft is delivered through the catheter to the site of deployment and then released from the catheter, whereupon it self-expands. Stent-grafts introduced in this manner are known as endoluminal stent-grafts.

A typical state of the art stent, such as disclosed in U.S. Pat. No. 4,655,771 to Wallsten or in U.K. Patent Number 1,205,743 to Didcott, is shown herein in prior art FIGS. 1, 1a, 2, and 2a. Didcott and Wallsten disclose a tubular body stent 10 composed of wire elements, e.g. 12, 13, each of which extends in a helical configuration with the centerline 14 of the stent 10 as a common axis. Half of the elements, e.g. 12, are wound in one direction while the other half, e.g. 13, are wound in an opposite direction. With this configuration, the diameter of the stent is changeable by axial movement of the ends 9, 11 of the stent. Typically, the crossing elements form a braid-like configuration and are arranged so that the diameter of the stent 10 is normally expanded as shown in FIGS. 1 and 1a. The diameter may be contracted by pulling the ends 9, 11 of the stent 10 away from each other as shown by the arrows 16, 18 in FIG. 2. When the ends of the body are released, the diameter of the stent 10 self-expands and draws the ends 9, 11 of the stent closer to each other. The contraction to stretching ratio and radial pressure of stents can usually be determined from basic braid equations. A thorough technical discussion of braid equations and the mechanical properties of stents is found in Jedweb, M. R. and Clerc, C. O., "A Study of the Geometrical and Mechanical Properties of a Self-Expanding Metallic Stent—Theory and Experiment", *Journal of Applied Biomaterials;* Vol. 4, pp. 77–85 (1993). In general, however, the contraction to stretching ratio is related to the axially directed angle α between the crossing elements 12, 13 in the expanded state as shown in FIG. 1. As explained in Didcott, the greater the magnitude of the angle α, the greater the amount of axial extension will be required to contract the diameter of the stent.

The ability of a stent to withstand radial forces is known in the art as "hoop strength". The hoop strength of both the Wallsten and the Didcott stents is relatively low. The Wallsten stent provides an improvement in hoop strength over Didcott by virtue of the higher pitch angle ($\alpha > 90°$). However, the higher pitch angle of the Wallsten stent renders the stent more difficult to place since substantial elongation is required to pull the stent down into a catheter introducer. Various designs have been advanced in efforts to increase stent hoop strength. These designs include the use of thicker wires, the use of more wires, and the use of paired wires. However, there are limitations to each of these designs. For example, if too many wires are used or if the wire diameter is too large, the stent will tend to demonstrate a taper on one end and a flare on the other end. This is detrimental to stent performance. Moreover, the use of numerous and/or thick wires often results in wire jamming when the stent is drawn down. This requires a larger introducer catheter which renders it more difficult to place in distal and tortuous vessels.

Apart from hoop strength, another problem with conventional stents is that the ends fray or become unbraided when they are cut. When this happens, it becomes difficult to load the stent into an introducer and it is possible for a stray wire end to penetrate the wall of the introducer. Similarly, an unbraided wire end can perforate the human vessel during or after placement.

Still another problem with the state of the art stents is that during normal use, even without cutting the stent, the ends of the stent tend to taper inward due to slippage of the wires and loss of braid structure. The tapered ends of a stent can perturb flow through the lumen of the stent and cause thrombosis. In addition, as the ends of an installed stent taper inward, the stent can become dislodged and may even be washed downstream through the vessel in which it was installed.

Yet, another problem with conventional Didcott or Wallsten stents is illustrated in prior art FIG. 3. When a stent 10 of this type is deployed in a vessel 20 having a bend 22, the pitch angle of the wired is increased in the portion of the stent 10 which traverses the bend 22. Hence, the diameter of the stent 10 at the center of the bend 22 is larger than the diameter of the stent 10 at its ends 9, 11, as the center of the stent stretches the vessel at the bend. This tends to alter the hemodynamics of the vessel.

Still another problem associated with these aforementioned stents is that the stent will flex continuously with each bolus of blood passing through the stent. The flexion continues until the stent is totally ingrown with biological tissue. During flexion, the wires undergo a scissors-like activity at the crossover points which can irritate tissue and adversely affect patency, especially in small diameter vessels such as the coronary arteries. Moreover, the points where the wires cross over each other are subject to abrasion when the stent is flexed in the vasculature. Severe abrasion manifests as wear in the wires which can ultimately lead to premature breakage of the wire components.

Another kind of (non-braided) stent is disclosed in European Patent Publication No. 0312852 to Wiktor. A Wiktor-type stent 30 is shown in prior art FIG. 4 in conjunction with a balloon catheter 31. The stent 30 is made of a single strand of zig-zag filament 32 which is helically wrapped around a mandril. While the filament 32 does not necessarily cross over itself, adjacent zig-zags, e.g. 34, 36, touch each other or come close to touching each other. One of the disadvantages of the Wiktor-type stent is that the zig-zag wire tends to expand non-uniformly when expanded in an artery by a balloon catheter. In addition, the non-braided stent can unfurl during maneuvering the balloon catheter in the vasculature which can cause placement problems as well as damage to the endothelium. In addition, the hoop strength of the Wiktor-type stent is relatively low.

Further disadvantages of conventional wire stents are that they are intrinsically thrombogenic and do not bind well to surface coatings due to the inertness of the metallic oxide layers on the wires.

SUMMARY OF THE INVENTION

It is therefore an object of the invention to provide a stent and a stent-graft with improved hoop strength.

It is also an object of the invention to provide a stent and a stent-graft which resist tapering and maintain flaring at the ends.

It is another object of the invention to provide a stent and a stent-graft which exhibit little or no abrasion of wires in the vasculature.

It is still another object of the invention to provide a stent and a stent-graft which maintain a substantially constant diameter when installed in the bend of a vessel.

In accord with these objects which will be discussed in detail below, the implantable stents and stent-grafts of the present invention include a conventional stent which is coated with a polymer such that the polymeric coating binds the crossover points of the wires, or, in the case of a Wiktor-type stent, binds adjacent zig-zags of wires without occluding the interstices of the stent lattice. Suitable coating polymers include polyurethane, polycarbonate urethane, polyurethane urea, silicone rubber, polyisobutylene copolymer (with styrene, etc.), polyolefin, polyester, glycolated polyester, polyamide, amorphous polyamide, combinations of the above and the like. Biodegradable polymers such as polyisobuterate, polyvalerate, polylactic acid, polyglycolic acid and combinations of these are also suitable. The major requirement for the polymer is that it can deform during loading of the stent into a catheter and that it has sufficient rebound or memory to return substantially to its original shape after the stent is deployed. The presently preferred polymer is an aromatic polycarbonate urethane of Shore hardness 80 A to 100 D; preferably Shore 55 D to 75 D. The polymer can be reacted in place on the stent without a solvent, such as two component polyurethanes, or silicone rubbers, or the reacted polymer can be dissolved in an appropriate solvent, for example, dimethylacetamide for the polyurethanes, toluene for the polyolefins, or heptane for the silicone rubbers. The concentration of solids to solvent is chosen for the specific process used to apply the polymer to the stent. For example, for spray coating, 5 to 10% solids by weight is preferred, while 7% to 13% solids is preferred for dip coating. Binary solvents such as dimethyacetamide and tetrahydrofuran can be used to accelerate dry times or spray build-up for polyurethanes.

In order to enhance bonding of the polymer to the stent wires, it may be desirable to prime the metallic stent prior to coating with polymer. Suitable primers include silane priming agents such as aminoethyaminopropyltriacytoxysilane. In addition to spraying and dipping, the polymer may be padded or spun onto the stent (or primed stent) and cured or dried to form the polymer adhesive, care being taken to avoid occlusion of the interstices of the stent lattice. Alternatively, the polymeric coating can be extruded onto the wire prior to fashioning the stent and once complete, the polymer can be melt-adhered to adjacent components.

The hoop strength of a polymer coated stent according to the invention is improved due to locking of the crossover points (or zig-zag points) and preventing free motion of the stent wires relative to each other. This also prevents sliding of the wires and hence abrasion of the wires at the crossover points as well as the scissor-like movement of the wires which causes irritation to tissue and adversely affects patency, especially in small diameter vessels such as coronary arteries. The polymer coating adds only a slight increase in wall thickness of the stent wires while increasing hoop strength significantly. The introduction profiles of polymer coated stents according to the invention are not appreciably increased. The polymeric coating also prevents ends from fraying or unbraiding when the stent is cut prior to deployment. In addition, the polymeric coating helps keep the ends of the stent flared to prevent the stent from migrating after deployment. This also provides a fluid dynamically favored entrance for blood flow. Moreover, the polymeric coating also maintains the stent in a cylindrical configuration throughout its length thereby preventing the ballooning and tapering phenomenon when deployed in the bend of an artery.

The presence of a polymer on the surface of the stent also allows for the dispensing of drugs through the polymer which may take the form of a surface modification or a drug eluting reservoir. For example, an anticoagulant such as heparin or the like can be bound to the polymer surface and automatically dispensed from the stent after deployment to prevent thrombosis. Alternatively, drugs such as antiinflammatory agents, steroids, or antimitotic drugs such as chemocompounds or radiomonic drugs can be eluted out of the stent coating after deployment. These drugs may prevent intimal hyperplasia. Still alternatively, radioactive materials containing beta or gamma emitters can be embedded in the polymer with their actinic radiation interfering with DNA replication thereby decreasing the incidence of hyperplasia. Genetically engineered drugs such as growth factors and the like can also be eluted from the coating material.

Additional objects and advantages of the invention will become apparent to those skilled in the art upon reference to the detailed description taken in conjunction with the provided figures.

DETAILED DESCRIPTION OF THE PREFERRED EMBODIMENTS

The invention will be described with reference to several examples in which a prior art stent is coated with a polymer in order to bind the wires of the stent at the crossing points (or zig-zag points) without occluding the interstices of the stent lattice.

EXAMPLE 1

Figure 5:
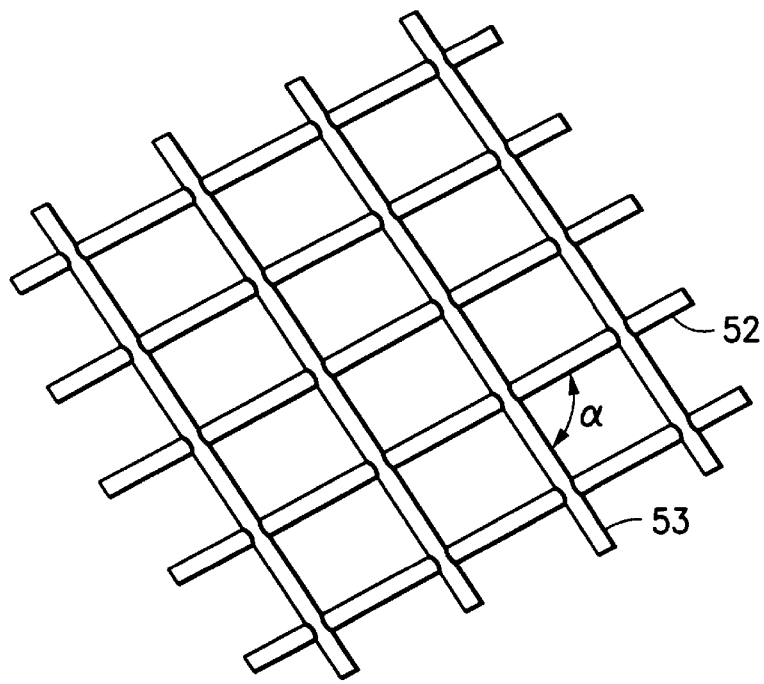
FIG. 5 is an enlarged broken side elevation view of a portion of a prior art braided stent.
Figure 6:
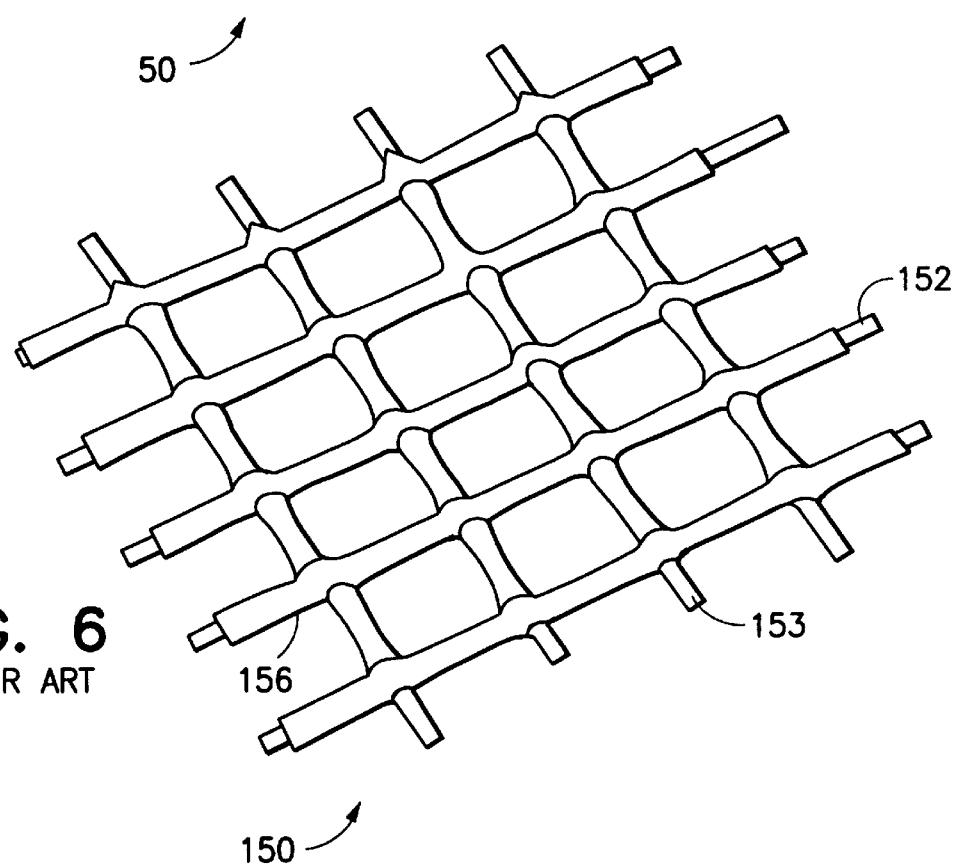
FIG. 6 is a view similar to FIG. 5 of a polymeric coated braided stent according to the invention.

Referring to FIGS. 5 and 6, a stent 50 is made of the Didcott design as shown in prior art FIG. 5. Each of the wires, e.g. 52, 53, is approximately eight millimeters in diameter and the wires are braided with a pitch angle of approximately 85°. The stent 50 has an outward hoop force for 50% compression of 0.11 lb, i.e., a radial load of 0.11 lbs is required to compress the stent radially 50%.

According to a first method of the invention, a polycarbonate urethane of Shore 55 D is dissolved in dimethylacetamide at a concentration of 5% solids content by weight. The mixture is sprayed onto the stent 50 and dried at 70° C. for ten minutes to create a coated stent 150 as shown in FIG. 6. Preferably, the spraying and drying is repeated several times in order to build up the surface coating of polycarbonate urethane, e.g. 156, on each of the wires, e.g. 152, of the stent 150. The load required to compress the stent 150 by 50% is tabulated below in Table 1 according to the number of coatings.

TABLE 1

| Number of spray coatings of 5% solids polycarbonate urethane 55D | Load (in lbs.) required to compress the stent 50% |
| --- | --- |
| 0 | 0.11 |
| 5 | 0.14 |
| 10 | 0.16 |
| 15 | 0.20 |

The coated stent 150 may be cut to size and loaded into a catheter without the ends fraying. The stent may then be delivered to the site of injury in the vascular system and deployed in the usual manner.

EXAMPLE 2

Figure 1:
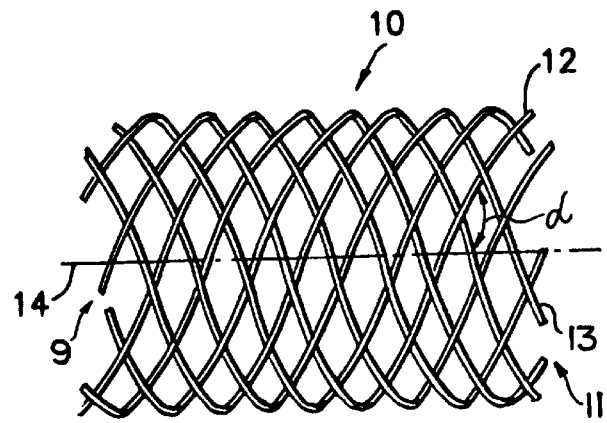
FIG. 1 is a broken side elevation view of a prior art braided stent expanded in a non-stressed position.
Figure 1A:
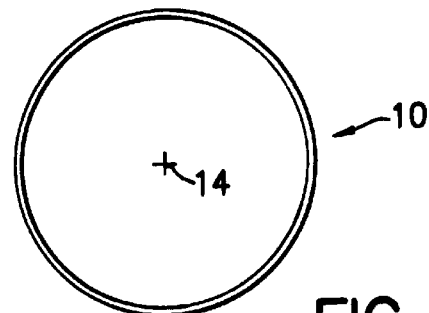
FIG. 1a is a cross sectional view along line 1A—1A of FIG. 1.
Figure 2:
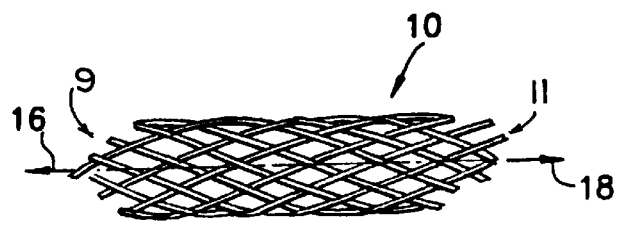
FIG. 2 is a broken side elevation view of a prior art stent of FIGS. 1 and 1a stretched and contracted.
Figure 2A:
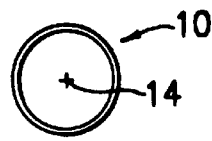
FIG. 2a is a cross sectional view along line 2A—2A of FIG. 2.
Figure 3:
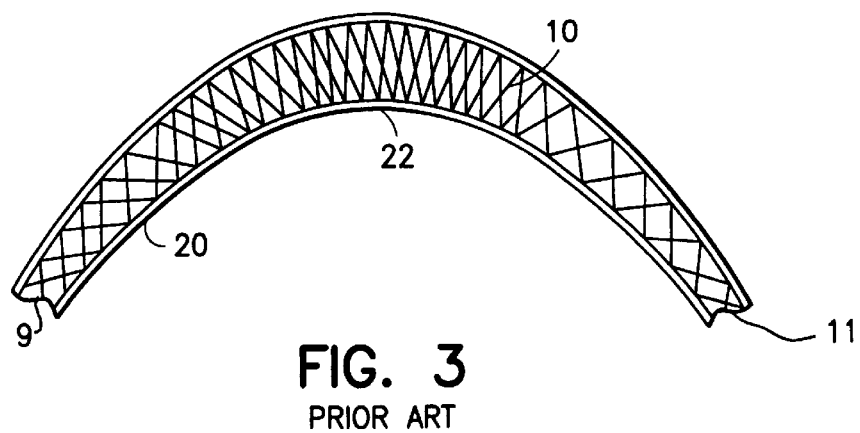
FIG. 3 is a broken side elevation view of a prior art stent deployed in the bend of an artery.
Figure 4:
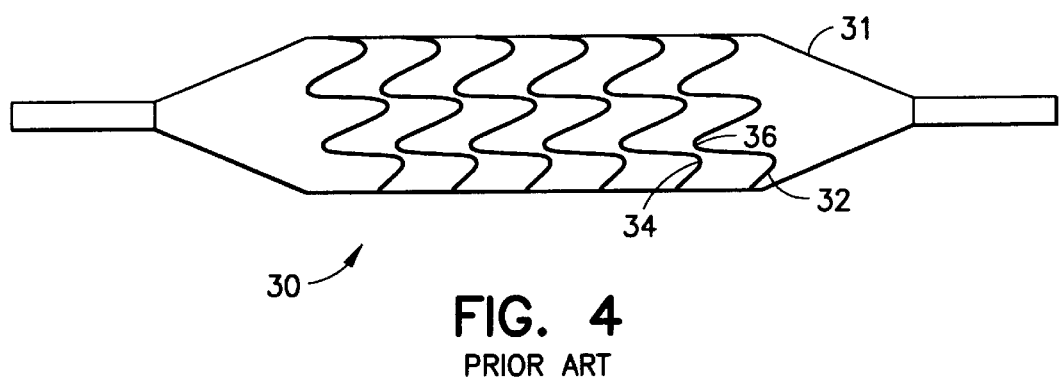
FIG. 4 is a view similar to FIG. 1 of a prior art undeployed zig-zag stent on a balloon catheter.
Figure 7:
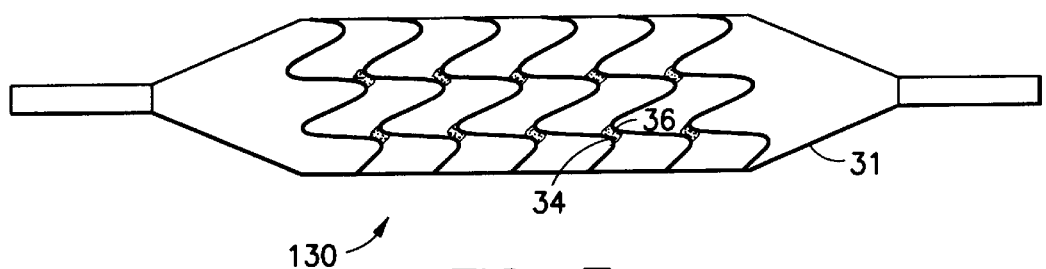
FIG. 7 is a view similar to FIG. 4 of a polymeric coated zig-zag stent according to the invention.

A balloon expandable stent 30 of the Wiktor design (FIG. 4) is placed on a mandril with adjacent zig-zags, e.g. 34, 36, touching each other. The stent 30 is sprayed with polycarbonate urethane of Shore 75 D hardness dissolved in dimethylacetamide at a concentration of 10% solids content by weight. The stent is dried and is sprayed and dried another five times. The resultant stent 130, shown in FIG. 7, is removed from the mandril and demonstrates a uniform cylindrical outline with higher hoop strength than the uncoated stent. The zig-zag wire comprising the stent is maintained in a uniform cylindrical outline. The stent is deployed with a balloon catheter 31 which is expanded to beyond the yield point of the polycarbonate urethane. When the stent is so deployed, it remains open in a uniform cylindrical outline.

EXAMPLE 3

The Didcott-type stent of FIG. 5 is spray coated (once or several times) with a biodegradable polymer comprised of a mixture of 50% polybuterate and 50% polyvalerate dissolved in chloroform. The resultant stent is rendered more rigid than the stent of Example 1, but softens appreciably after implantation in the body.

EXAMPLE 4

Figure 8:
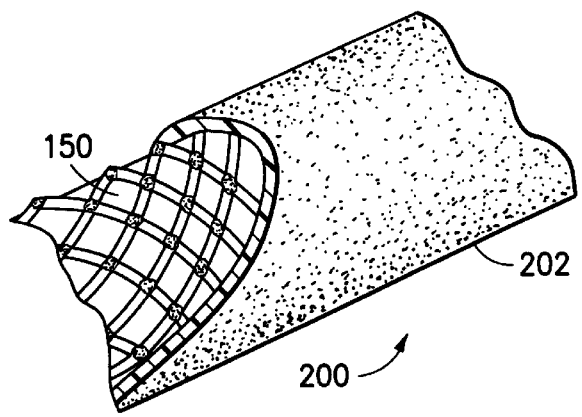
FIG. 8 is a broken perspective view of a polymeric coated braided stent-graft according to the invention.

The coated stent 150 described in Example 1 and shown in FIG. 6 is attached to a vascular graft as described in Dereume Belgium Patent No. 112,774 and shown in FIG. 8 to form an endoluminal graft 200. The vascular graft 202 may be applied to the interior of the stent or to the exterior of the stent as shown in FIG. 8. The endoluminal graft 200 is implanted in a tortuous artery where it assumes the shape of the artery without the ends becoming tapered or the center ballooning.

EXAMPLE 5

The coated stent 150 described in Example 1, with ten coatings of polyurethane is immersed in a solution containing 5% phospholipid in water. A thin layer of phospholipid is thereby bound to the surface of the polymeric coating. A stent made according to this example was placed in the coronary artery of a dog and demonstrated little thrombus build-up due to the hemocompatible nature of the phospholipid surface.

EXAMPLE 6

In a solution of dimethyl acetamide and 5% polycarbonate urethane of Shore 50 D hardness, the drug 5-fluorouracil is added (10% weight of the drug to the weight of polycarbonate urethane). The lacquer containing the drug is dip-coated onto a stent and allowed to dry. The drug eluting polymer-coated stent according to this example was implanted into the coronary artery of a dog where the drug was slowly released. The eluted drug interfered with the reproduction of DNA in the coronary artery thereby preventing intimal hyperplasia of the vessel.

EXAMPLE 7

Figure 9:
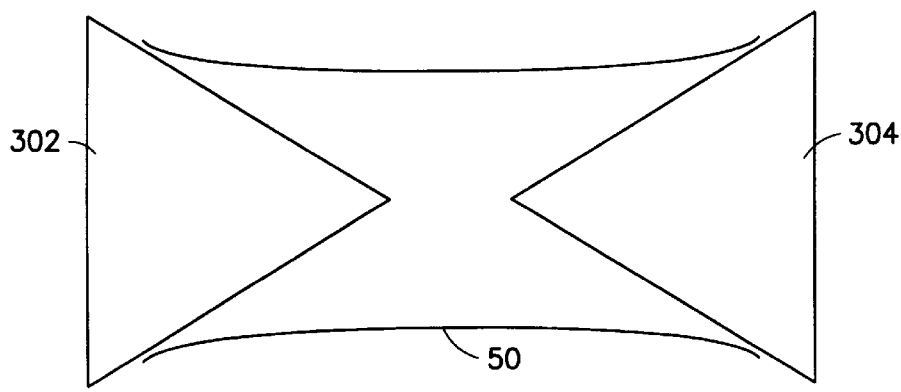
FIG. 9 is a schematic sectional view of a polymeric coated stent according to the invention with conical inserts flaring the ends of the stent.

A Didcott-type stent such as that used in Example 1 is placed on a mandril having two conical inserts as shown schematically in FIG. 9. The conical inserts 302, 304 are forced into the ends of the stent 50 such that the ends are flared. The stent is then spray coated with 15 layers of polycarbonate urethane (5% solids) and dried and removed from the mandril. The stent demonstrates flares on each end.

EXAMPLE 8

A coated stent 150 (FIG. 6) made according to Example 1 with ten layers of polycarbonate urethane is placed on a mandril having two conical inserts. The conical inserts are forced into the ends of the stent such that the ends are flared. The stent and mandril are then placed in an oven at 170°–200° C. where the polycarbonate urethane is partially melted. The stent and mandril are then cooled to room temperature at which point the conical inserts are removed from the stent. The stent now demonstrates flared ends with high hoop strength on the ends.

EXAMPLE 9

An Elgiloy™ wire self-expanding stent is primed by dipping it into a solution of 2% aminopropylaminoethyltrimethoxysilane dissolved in a 95%/5% ethanol-water mixture. The primed stent is then dried overnight at room temperature and placed on a rotating mandril. The stent is spray-coated and dried three times with a solution containing 9 grams of polycarbonate urethane of 75 D durometer, 1 gram of polycarbonate urethane of 55 D durometer, 75 grams of dimethylacetamide and 75 grams of tetrahydrofuran. The dried stent has a hoop strength four times higher than the initial hoop strength of the uncoated stent. In lieu of am Elgiloy™ wire, the wire may be Phyno™ or 316 LV stainless steel.

EXAMPLE 10

A porous spun polycarbonate urethane liner of melting point 160° C. is made by spinning five hundred passes from a thirty orifice spinneret of polymer onto a stainless steel mandril at 1,000 RPM with a wrap angle of 50°. The liner is cured in an oven at 110° C. overnight. A stent is dip-coated with 5% polycarbonate urethane of 75 D hardness and with a melting point 240° C. in tetrahydrofuran and dried. The 75 D-coated stent is again dipped into another solution of polycarbonate urethane but of 80 A hardness and of 160° C. melting point and dried. An additional ten passes of fiber are spun over the liner and while wet, the 75 D- and 80 A-coated stent is placed over the liner and the assembly placed in an oven at 120° C. where the wet outer layers on the liner are melted and bonds the stent to the liner. The stent-graft thus formed has a higher hoop strength that without the 75 D coating.

EXAMPLE 11

The stent-graft assembly of Example 10 is further reinforced by placing it back on the spinning machine where an additional one hundred passes of fiber are spun over the stent. While the fibers are wet, a soft silicone roller is rolled over the stent thereby pressing the fibers through the picks of the stent and bonding them to the inner liner. The stent-graft thus formed demonstrates a much better attachment of the liner to the stent.

EXAMPLE 12

Tantalum wire of 0.004" diameter is pulled through an extruder die where a thin layer (0.001") of fluorinated ethylene propylene (FEP) polymer of melting point 420° C. is extruded over the wire. The wires are formed into a zig-zag pattern according to Wiktor and then wound into a helical geometry with adjacent zig-zags touching each other. The stent is then heated to 420° C. where the FEP melts and when cooled adheres to adjacent zig-zags. The cooled assembly is removed from the mandril and demonstrates a uniform design with higher hoop strength than the uncoated stent. The zig-zag wire comprising the stent is maintained uniform. The stent is then balloon expanded beyond the yield strength of the FEP where it remains open in a uniform manner.

There have been described and illustrated herein several embodiments of implantable stents and stent-grafts having wires which are coated with a polymer at their crossing points or zig-zag vertices. While particular embodiments and examples of the invention have been described, it is not intended that the invention be limited thereto, as it is intended that the invention be as broad in scope as the art will allow and that the specification be read likewise. Thus, while particular conventional stents have been disclosed in conjunction with the method of the invention, it will be appreciated that other stents could be subjected to the inventive methods disclosed herein. Also, while specific examples of polymeric coatings have been described, it will be recognized that other polymers having similar properties could be used with similar results obtained. Furthermore, while specific methods of applying the coating have been shown, such as dipping and spraying, other methods could be used. For example, the polymer could be applied using electro-spraying where a potential difference is applied between the spray nozzle and the stent. Moreover, while particular examples have been disclosed in reference to drug delivery via the polymeric coating, it will be appreciated that other types of drugs could be used as well. It will therefore be appreciated by those skilled in the art that yet other modifications could be made to the provided invention without deviating from its spirit and scope as so claimed.

We claim:

1. A prosthesis comprising:
   a) a radially and axially flexible substantially cylindrical body formed from a plurality of wire filaments having crossing points defining a lattice of interstices between wire filaments, said wire filaments being coated with a polycarbonate urethane polymer having a melting point of approximately 240° C. substantially continuously alone substantially their entire lengths and at said crossing points so that said wire filaments are bound to each other by said polymer at said crossing points and said interstices of said lattice are not substantially occluded by said polymer; and
   b) a porous vascular graft attached to said body, said porous vascular graft comprising a spun polycarbonate urethane liner having a melting point of approximately 160° C.

2. A prosthesis comrising:
   a radially and axially flexible substantially cylindrical body formed from a plurality of wire filaments having crossing points defining a lattice of interstices between wire filaments, said wire filaments being coated with a polymer at said crossing points so that said wire filaments are bound to each other by said polymer at said crossing points and said interstices of said lattice are not substantially occluded by said polymer, wherein
   said wire filaments are coated by applying a polymeric solution containing a biodegradable mixture of polybuterate and polyvalerate dissolved in chloroform to the crossing points and allowing said polymeric solution to cure such that said crossing points are bound to each other by said polymer.

3. A prosthesis comprising:
   a radially and axially flexible substantially cylindrical body formed from a plurality of wire filaments having crossing points defining a lattice of interstices between wire filaments, said wire filaments being coated with a polymer at said crossing points so that said wire filaments are bound to each other by said polymer at said crossing points and said interstices of said lattice are not substantially occluded by said polymer, wherein
   said wire filaments are coated by dipping said substantially cylindrical body in a priming solution of 2% aminopropylaminoethyltrimethoxysilane dissolved in a substantially 95%/5% mixture of ethanol and water, substantially drying the dipped cylindrical body, and then applying a polymeric solution to said crossing points and allowing said polymeric solution to cure such that said crossing points are bound to each other by said polymer.

* * * * *

UNITED STATES PATENT AND TRADE MARK OFFICE
CERTIFICATE OF CORRECTION

PATENT NO. : 5,968,091
DATED : October 19 1999
INVENTOR(S) : Leonard Pinchuk, et al.

It is certified that error appears in the above-identified patent and that said Letters Patent is hereby corrected as shown below:

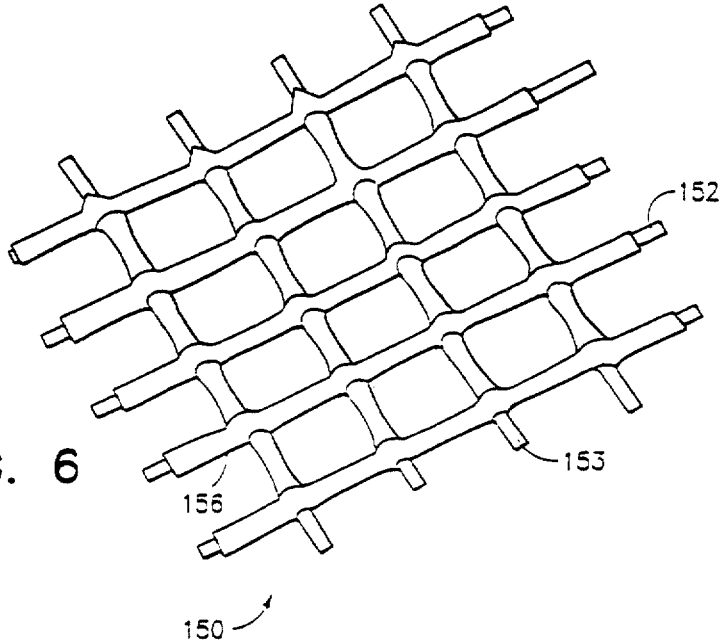

FIG. 6

Signed and Sealed this

Fourteenth Day of November, 2000

*Attest:*

Q. TODD DICKINSON

*Attesting Officer*     *Director of Patents and Trademarks*